United States Patent [19]

Lee

[11] 3,940,450

[45] Feb. 24, 1976

[54] PREPARATION AND RECOVERY OF ETHERS

[75] Inventor: Kung-You Lee, Wappingers Falls, N.Y.

[73] Assignee: Texaco Inc., New York, N.Y.

[22] Filed: Dec. 16, 1974

[21] Appl. No.: 533,057

[52] U.S. Cl................. 260/614 A; 203/43; 203/44; 203/45; 203/46; 203/70; 203/81; 203/82; 203/83; 203/91; 203/92; 203/93; 260/616; 260/643 R; 260/643 D
[51] Int. Cl.².................. C07C 41/12; C07C 41/00
[58] Field of Search.................... 203/70, 43, 44–46, 203/81–83, 91–93; 260/614 A, 614 R, 616

[56] References Cited

UNITED STATES PATENTS

| | | | |
|---|---|---|---|
| 3,119,766 | 1/1964 | Voltz | 260/614 A X |
| 3,846,088 | 11/1974 | Brown et al. | 260/614 A X |

FOREIGN PATENTS OR APPLICATIONS

| | | | |
|---|---|---|---|
| 957,000 | 4/1964 | United Kingdom | 260/614 A |

*Primary Examiner*—Howard T. Mars
*Attorney, Agent, or Firm*—T. H. Whaley; C. G. Ries; Carl G. Seutter

[57] ABSTRACT

Methyl tertiary butyl ether may be recovered from etherification reaction effluent by azeotropic distillation to recover methanol-ether azeotrope overhead which latter is azeotropically distilled in the presence of n-pentane to give pure ether bottoms substantially free of water and methanol.

14 Claims, 1 Drawing Figure

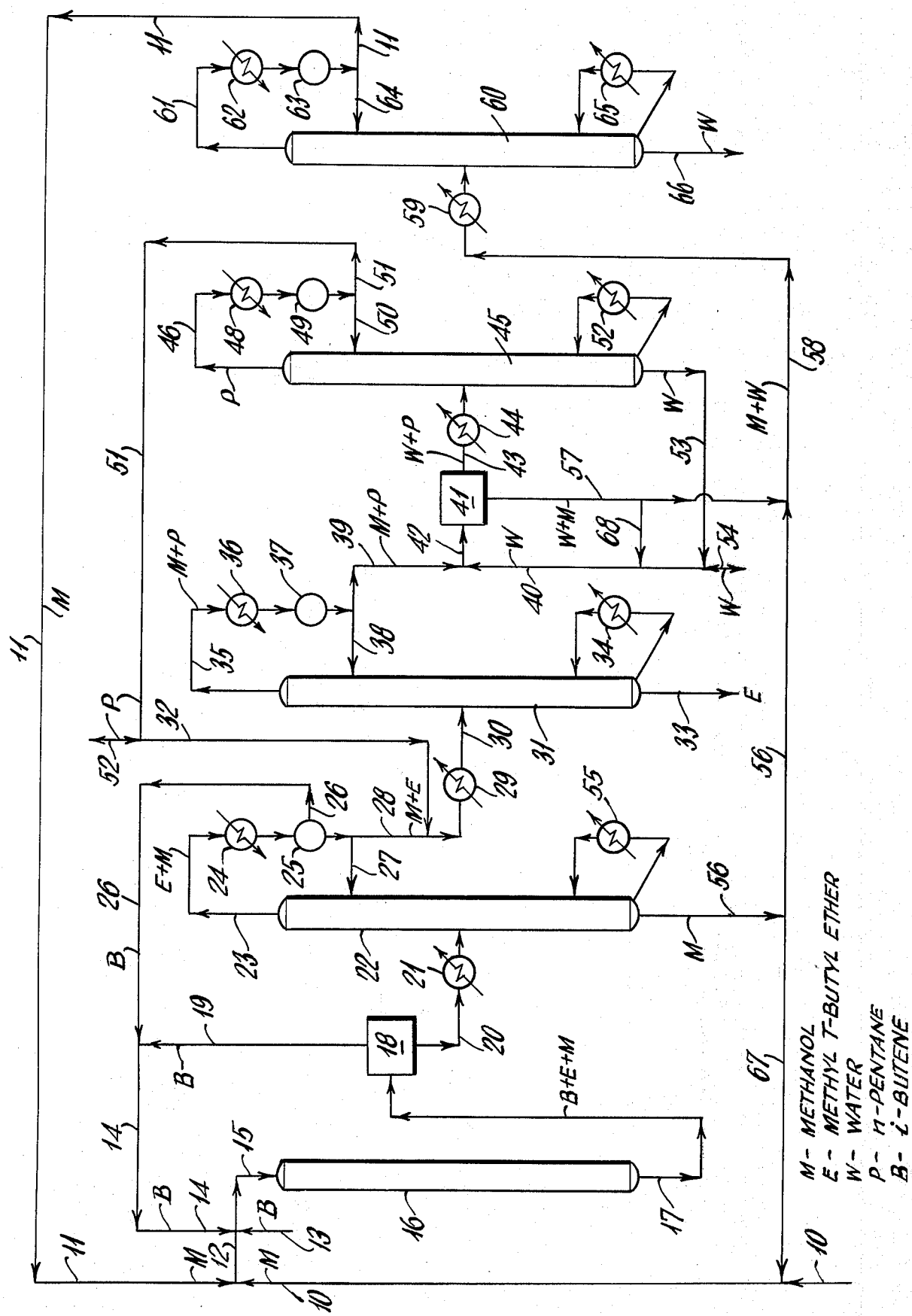

PREPARATION AND RECOVERY OF ETHERS

FIELD OF THE INVENTION

This invention relates to the preparation of ethers. More particularly it relates to the preparation of unsymmetrical ethers in high yield and purity.

BACKGROUND OF THE INVENTION

As is well known to those skilled in the art, ethers, including unsymmetrical ethers, may be prepared by reacting an alcohol with another alcohol to form the desired product. The reaction mixture, containing catalyst and/or condensing agent, may be separated and further treated to permit attainment of desired product. Such further treatment commonly includes one or more distillation operations.

It is an object of this invention to provide a process for preparing ethers. Other objects will be apparent to those skilled in the art from the following description.

SUMMARY OF THE INVENTION

In accordance with certain of its aspects, the novel method of this invention for preparing a desired product ether may comprise distilling a reaction mixture containing methanol and methyl t-butyl ether in a first distilling operation thereby forming first azeotrope overhead containing methanol and methyl t-butyl ether and first azeotrope bottoms containing methanol;

distilling said first azeotrope overhead containing methanol and methyl t-butyl ether in a second distillation operation in the presence of n-pentane thereby forming second azeotrope overhead containing methanol and n-pentane and second azeotrope bottoms containing desired product methyl t-butyl ether; and withdrawing said second azeotrope bottoms containing desired product methyl t-butyl ether.

DESCRIPTION OF THE INVENTION

Preparation of the product ether of this invention may be carried out typically be reacting methanol with isobutylene (i.e. isobutene). Although the reactants may be impure, it is preferred that they be of reasonable purity. Hydrocarbon impurities, if present eg in the isobutene stream may readily be removed after etherification.

Reaction may be carried out utilizing the following reaction conditions:

TABLE

| Conditions | Broad Range | Preferred Range | Preferred Value |
|---|---|---|---|
| Temperature °F. | 100–300 | 150–250 | 200 |
| Pressure psig | 50–750 | 50–500 | 300 |
| Methanol (parts) | 150–1500 | 150–600 | 500 |
| Isobutene (parts) | 150–700 | 150–1500 | 300 |

The charge isobutene may be present as a portion of a hydrocarbon stream which contains inerts such isobutane which do not react during the course of reaction; when this is the case they will be removed, as by distillation, from the product stream.

It is a particular feature of the process of this invention that the mole ratio of the methanol to the isobutene may be at least about 0.8. It will be found however that the advantages inherent in the process may be attained to a greater degree if this ratio is greater than 1 and preferably 1.2–4.0, say 2.0. Presence of the excess of e.g. methanol facilitates purification of the desired unsymmetrical ethers.

Etherification may be preferably carried out in the presence of a solid resin etherification catalyst. These catalysts are preferably relatively high molecular weight carbonaceous materials containing at least one —SO$_3$H group as the functional group. Typical of these catalysts are the sulfonated coals ("Zeo-Karb H," "Nalcite X" and "Nalcite AX") produced by the treatment of bituminous coals with sulfuric acid. These materials are usually available in a neutralized form and in this case must be activated to the hydrogen form by treatment with a strong mineral acid such as hydrochloric acid, followed by water washing to remove sodium and chloride ions prior to use.

The sulfonated resin type catalysts are preferred for use in the present invention. These catalysts include the reaction products of phenol-formaldehyde resins and sulfuric acid ("Amberlite IR-1", "Amberlite IR-100", and "Nalcite MX"). Also useful are the sulfonated resinous polymers of coumarone-indene with cyclopentadiene; sulfonated polymers of coumarone-indene with furfural; sulfonated polymers of coumarone-indene with cyclopentadiene and furfural; and sulfonated polymers of cyclopentadiene with furfural.

The most preferred cationic exchange resins are strongly acidic exchange resins consisting essentially of sulfonated polystyrene resin, for instance, a divinylbenzene cross-linked polystyrene matrix having 0.5–20% and preferably 4–16% of copolymerized divinylbenzene therein, bearing ionizable or functional nuclear sulfonic acid groups. These resins are manufactured and sold commercially under various trade names such as "Dowex 50", "Nalcite HCR" and Amberlyst 15". As commercially obtained they have a solvent content of about 50% and can be used as is or the solvent can be removed first. The resin particle size may typically be 10 to 50 mesh (U.S. Sieve Series).

The reaction may be carried out in either a stirred slurry reactor or in a fixed bed continuous flow reactor. The catalyst concentration should be sufficient to provide the desired catalytic effect. Generally in a stirred reactor, catalyst concentration should be 0.1–10% (dry basis) by weight of the reactor contents, 0.2 to 5% being the preferred range.

There may thus be added to the reaction operation in the preferred embodiment, 500 parts of the methanol and 500 parts of isobutene. During reaction, the desired product methyl terbutyl ether is formed by reaction of methanol and isobutene. Etherification is preferably carried out at 100°F–300°F, preferably 150°F–250°F, say 200°F; and the pressure may be 50–750 psig, preferably 50–500 psig, say 300 psig. The typical crude product stream may contain 214–414 parts, say 273 parts of methanol, 0–350 parts, say 102 parts of isobutene, and 236–786 parts, say 625 parts of methyl tertiary butyl ether.

The crude product stream so obtained is passed to a separation operation wherein 0–100 parts, say 10 parts of isobutene are flashed off.

In the preferred embodiment, this isobutene is recovered and recycled to the etherification operation. If the system contains undesirable volatile components, these may be separated out at this point.

The flashed crude product contains substantially only methanol, isobutene, and methyl t-butyl ether; and because of the control of the mole ratio of methanol to isobutene in the etherification reaction, the content of methanol in the flashed ether stream is typically at least 15%, and more typically 20 – 50%, preferably 20 – 30%, say 27%. At the pressure of operation of the first azeotropic distilling operation, the quantity of methanol in an azeotropic mixture with methyl tertiary butyl ether is about 15%; and thus there is preferably at least this much methanol present in the flashed crude product.

Flashed crude product i.e. separated etherification reaction mixture which has been stripped or denuded of isobutene is heated to 120°F–150°F, preferably 125°F–135°F, say 130°F and passed to first distilling operation at 0–40 psig, preferably 0–10 psig, say 0 psig.

Overhead withdrawn from the first distilling operation typically at 115°F–125°F, say 118°F is an azeotrope of methanol and methyl tertiary butyl ether containing eg at atmospheric pressure, say 15% of methanol. This stream is condensed; the non-condensibles (isobutene) are recovered and may be recycled to etherification.

After return of pumped reflux to the first azeotropic distillation, the azeotrope condensate typically containing 40–140 parts, say 110 parts of methanol and 236–786 parts, say 625 parts of ether, are heated to 100°F–110°F, say 105°F and passed to a second azeotropic distillation operation. To this second azeotropic distillation there is also added normal pentane as azeotroping agent. Although the n-pentane need not be pure, in the preferred embodiment, it is so. Preferably 400–1540 parts, say 1100 parts of n-pentane are admitted. This corresponds to 10–11 parts, say 10.5 parts of n-pentane per part of methanol. Preferably at least about 10 parts of n-pentane will be admitted per part of methanol.

Charge to the second azeotropic distillation is admitted there to at 0 – 20 psig, preferably say 0 psig. Bottoms, withdrawn at 130°F–138°F, preferably 130°F–135°F, say 134°F, include 236–786 parts, say 625 parts of product methyl tertiary butyl ether of high purity.

Overhead from the second azeotropic distillation, recovered at 80°F–90°F, preferably 85°F–90°F, say 87°F and condensed, includes (after separation and return to the tower of pumped reflux) preferably 40–140 parts, say 110 parts of methanol and 400–1540 parts, say 1112 parts of pentane. The second azeotropic overhead contains 90%–92%, say 91% n-pentane and 8%–10%, say 9% methanol at preferred operating pressure of 0 psig. This stream is passed to a contacting operation. Here it is contacted at 40°F–120°F, say 70°F with 200 – 1000 parts, preferably 300–600 parts, say 400 parts of aqueous extraction liquid, typically water which may contain eg small quantities of methanol.

Raffinate, withdrawn from the contacting operation, typically includes preferably 400–1540 parts, say 1110 parts of n-pentane, preferably 1 – 5 parts say 1 parts of water, and 5 – 25 parts, preferably less than 5 parts of methanol. This stream is heated to preferably 90°F, say 97°F and passed to a fractionation operation.

Fractionation is carried out to give as fractionator overhead at preferably 90°F–100°F, say 97°F, a substantially pure n-pentane steam. After condensation and return of pumped reflux to the fractionator, the net product is found to include preferably 400–1540 parts, say 1110 parts of n-pentane, This stream is preferably recycled at least in part to the second azeotropic distillation operation.

Fractionator bottoms, after reboiling, as say 100°F include say 2 parts of water and 5 parts of methanol. This stream is preferably recycled at least in part to the contacting operation.

The bottoms from the first azeotropic distillation, after reboiling, are withdrawn at 150°F – 160°F, say 155°F in amount of 70–370 parts, say 163 parts. This stream is preferably combined with the aqueous extract from the extraction operation to form a stream containing water.

The methanol-water stream is heated to 140°F – 150°F, preferably 145°F – 155°F, say 150°F and passed to a rectification operation. Rectifier bottoms, recovered at 200°F – 215°F, say 212°F is substantially pure water.

Rectifier overhead recovered at 145°F–150°F, say 149°F, after condensation and return of pumped reflux, includes substantially pure methanol. Net overhead is preferably recycled in whole or in part to the etherification operation.

It is a particular feature of the process of this invention that it permits ready production and recovery of desired product ether in high purity. The process readily permits product ether to be obtained which is substantially free of methanol and water. These components are undesirable because when the product ether is blended into gasoline formulations, (a) methanol will extract water from tank bottoms and (b) water will cause the gasoline to be hazy.

Attempts to remove water from product ether have heretofore not been possible by simple distillation. Removal of methanol from product ether has also been difficult. The solubility of the ether in water also contributes to the problem. In the instant process, no water washing of streams containing product ether is necessary; and thus losses of ether are minimized.

DESCRIPTION OF THE SPECIFIC EMBODIMENT

Practice of the process of this invention may be apparent to those skilled in the art from the following wherein, as elsewhere in this description, all parts are parts by weight unless otherwise specified. It will be apparent that the drawing is schematic and may not show details of the processing technique including eg pumps, vessels, heat exchangers, etc.

In the drawing, the lines are identified as containing the following components:

| | |
|---|---|
| M | methanol |
| E | methyl t-butyl ether |
| W | water |
| P | n-pentane |
| B | isobutene |

It will be apparent that certain lines bearing a particular label may contain small amounts of other components. For example line 23, bearing the legend E + M, may contain small amounts of isobutene.

In the drawing which represents practice of a preferred embodiment of the process of this invention, 240 parts of fresh methanol are admitted through line 10 together with 260 parts of recycle methanol admitted through line 11 to form in line 12 a stream containing 500 parts (15.6 moles) of substantially anhydrous methanol. There are also admitted 398 parts of fresh isobutene through line 13 and 102 parts of recycle isobutene through line 14 to form in line 15 a stream containing 500 parts (8.9 moles) of isobutene together with the methanol.

Charge in line 15 is admitted to etherification operation 16 wherein it contacts 87 parts of Amberlyst 15 Sulfonic Acid Resin ion exchange catalyst (Rohm and Haas Inc) at a WHSV of 11.5. Amberlyst 15 is a cationic, strongly acidic, exchange resin containing a sulfonated polystyrene resin crosslinked with divinyl benzene. Reaction mixture leaves the etherification operation at 200°F and 300 psig.

Reaction mixture i.e. crude product in line 17 contains 273 parts of methanol, 102 parts of isobutene, and 625 parts of methyl t-butyl ether. This stream is passed to separation operation 18, preferably a flashing operation wherein 10 parts of isobutene are flashed off and passed through line 19 to line 14. Flashed crude product is passed through line 20, heated to 130°F in heat exchanger 21 and admitted to first distillation tower 22 at 0 psig.

First azeotrope overhead is withdrawn from first distillation tower 22 at 118° F through overhead line 23, condensed in condenser 24, and collected in drum 25. Isobutene in amount 92 parts may be withdrawn through line 26 and passed to line 14. Pumped reflux may be passed through line 27; and net product azeotrope overhead in line 28 may contain 110 parts of methanol and 625 parts of methyl t-butyl ether.

First azeotrope overhead in line 28 is passed through exchanger 29 and line 30 to second distillation operation 31. Also admitted to line 28 through line 32 is 1112 parts of n-pentane; this total stream in line 28 is heated in exchanger 29 and admitted to tower 31 at 0 psig and 100°F.

Second azeotrope bottoms are withdrawn at 134°F through line 33, after reboiling in reboiler circuit 34, in amount of 625 parts of substantially pure methyl t-butyl ether containing less than 0.015 parts of water and less than 0.005 parts of methanol. This represents a yield of 80% of product ether of purity greater than 99%.

Second azeotrope overhead recovered in line 35 at 87°F is condensed in condenser 36 and collected in drum 37. Pumped reflux is passed through line 38. Net product in line 39 includes 110 parts of methanol 1112 parts of n-pentane.

The net product second azeotrope overhead in line 39 is contacted at 70° F and 0 psig with 400 parts of water (admitted through line 40) in contacting operation 41 to which the combined streams are admitted through line 42. Raffinate from operation 41, containing 1110 parts of n-pentane, 2 parts of water, and 5 parts of methanol, is withdrawn through line 43, heated to 97°F in heat exchanger 44 and passed to fractionation operation 45 at 0 psig.

Fractionation overhead is withdrawn at 97°F through line 46, condensed in condenser 48, and collected in vessel 49. Pumped reflux is passed through line 50. Net product fractionation overhead in line 51, including 1110 parts of n-pentane, 0 parts of water, and 0 parts of methanol, is passed through line 51 to join with the stream in line 32. n-pentane may be withdrawn, or more commonly added through line 52 to satisfy the needs of the system.

Fractionator bottoms containing water, after reboiling in reboiler circuit 52, are withdrawn at 100°F through line 53 in amount of 2 parts of water, and 5 parts of methanol. Water may be withdrawn and/or added through line 54; and the total water from line 53 and 54 may be passed through line 40 to contacting operation 41.

First azeotrope bottoms, after reboiling in reboiler circuit 55 are withdrawn at 155°F in line 56 in amount of 163 parts of methanol. (If the operation is carried out so that the methanol is pure, it may be recycled through line 67 to line 10.) To this stream in line 56 is added 398 parts of water and 110 parts of methanol from line 57 and the total passed through line 58 and heat exchanger 59 wherein it is heated to 150°F. (It may be desirable to recycle at least a portion of the stream in line 57 through line 68 to operation 41 until the methanol content thereof has increased. The so-heated stream is introduced to rectification operation 60 at 0 psig.

Overhead from rectification operation 60, withdrawn at 149°F and 0 psig through line 61, is condensed in condenser 62, and collected in drum 63. Pumped reflux is passed through line 64. Net product 260 parts of substantially pure methanol is passed through line 11 as recycle methanol to etherification operation 16 via lines 12 and 15.

Bottoms from rectifier 60, after reboiling in reboiler circuit 65, as withdrawn at 215°F through line 66, include 398 parts of water; this may be recycled if desired, in whole or in part to line 40 through line 54.

Although this invention has been illustrated by reference to specific embodiments, it will be apparent to those skilled in the art that various changes and modifications may be made which clearly fall within the scope of this invention.

I claim:
1. The method which comprises
   distilling a reaction mixture containing methanol and methyl t-butyl ether in a first distilling operation thereby forming first azeotrope overhead containing methanol and methyl t-butyl ether and first azeotrope bottoms containing methanol;
   distilling said first azeotrope overhead containing methanol and methyl t-butyl ether in a second distillation operation in the presence of n-pentane thereby forming second azeotrope overhead containing methanol and n-pentane and second azeotrope bottoms containing desired product methyl t-butyl either; and
   withdrawing said second azeotrope bottoms containing desired product methyl t-butyl ether.
2. The method claimed in claim 1 wherein in said reaction mixture the mole ratio of methanol to isobutene is at least about 0.8.
3. The method claimed in claim 1 wherein in said reaction mixture the mole ratio of methanol to isobutene is greater than 1.
4. The method claimed in claim 1 wherein said first distilling operation is carried out at 0 – 5 psig.
5. The method claimed in claim 1 wherein said first azeotrope overhead contains 83 – 87% methyl tertiarybutyl ether and 13 % – 17 % methanol.
6. The method claimed in claim 1 wherein said first azeotrope bottoms consists essentially of methanol.
7. The method claimed in claim 1 wherein the charge to said second distillation operation includes 10 – 11 parts of n-pentane per part of methanol.
8. The method claimed in claim 1 wherein the charge to said second distillation operation includes at least 10 parts of n-pentane per part of methanol.

9. The method claimed in claim 1 wherein said second azeotrope overhead contains 90 – 92 % n-pentane and 8 – 10 % methanol.

10. The method claimed in claim 1 wherein said second azeotrope overhead contains about 91 % n-pentane and 9 % methanol.

11. The method claimed in claim 1 wherein said second azeotrope bottoms consists essentially of methyl tertiary-butyl ether.

12. The method which comprises
distilling a reaction mixture containing methanol and methyl t-butyl ether in a first distilling operation thereby forming first azeotrope overhead containing methanol and methyl t-butyl ether and first azeotrope bottoms containing methanol;
distilling said first azeotrope overhead containing methanol and methyl t-butyl ether in a second distillation operation in the presence of n-pentane thereby forming second azeotrope overhead containing methanol and n-pentane and secnd azeotrope bottoms containing desired product methyl t-butyl ether;
rectifying at least a portion of said first azeotrope bottoms containing methanol and at least a portion of said aqueous extract containing water and methanol thereby forming a rectification overhead containing methanol;
recovering said rectification overhead containing methanol;
withdrawing said second azeotrope bottoms containing desired product methyl t-butyl ether;
contacting said second azeotrope overhead containing methanol and n-pentane in a contacting operation with water thereby forming aqueous extract containing water and methanol and raffinate containing n-pentane;
fractionating said raffinate thereby forming fractionation overhead containing n-pentane and fractionation bottoms containing water; and
passing at least a portion of said fractionation overhead containing n-pentane to said second distillation operation.

13. The method which comprises
reacting methanol and isobutene in the presence of a solid resin etherification catalyst thereby forming a reaction mixture including unreacted methanol, unreacted isobutylene, and product methyl t-butyl ether;
separating said unreacted isobutene from said reaction mixture thereby forming a separated reaction mixture containing unreacted methanol and product methyl t-butyl ether;
distilling said separated reaction mixture containing methanol and methyl t-butyl ether in a first distilling operation thereby forming first azeotrope overhead containing methanol and methyl t-butyl ether and first azeotrope bottoms containing methanol;
distilling said first azeotrope overhead containing methanol and methyl t-butyl ether in a second distillation operation in the presence of n-pentane thereby forming second azeotrope overhead containing methanol and n-pentane and second azeotrope bottoms containing desired product methyl t-butyl ether;
withdrawing said second azeotrope bottoms containing desired product methyl t-butyl ether;
contacting said second azeotrope overhead containing methanol and n-pentane in a contacting operation with water thereby forming aqueous extract containing water and methanol and raffinate containing n-pentane;
fractionating said raffinate thereby forming fractionation overhead containing n-pentane and fractionation bottoms containing water.

14. The method which comprises
reacting methanol and isobutene in the presence of a solid resin etherification catalyst thereby forming a reaction mixture including unreacted methanol, unreacted isobutylene, and product methyl t-butyl ether;
separating said unreacted isobutene from said reaction mixture thereby forming a separated reaction mixture containing 20 – 50% of unreacted methanol and 40% – 70 % of product methyl t-butyl ether;
distilling said separated reaction mixture in a first distilling operation thereby forming first azeotrope overhead containing 13 – 17 % of methanol and 83 % – 87 % of methyl t-butyl ether and first azeotrope bottoms containing methanol;
distilling said first azeotrope overhead containing methanol and methyl t-butyl ether in a second distillation operation in the presence of 10 – 11 parts of n-pentane per part of methanol thereby forming second azeotrope overhead containing 8% – 10% of methanol and 90–92% of n-pentane and second azeotrope bottoms consisting essentially of desired product methyl t-butyl ether;
withdrawing said second azeotrope bottoms containing desired product methyl t-butyl ether;
contacting said second azeotrope overhead containing methanol and n-pentane in a contacting operation with 3 – 4 parts of water per part of methanol thereby forming aqueous extract containing water and methanol and raffinate containing n-pentane;
fractionating said raffinate thereby forming fractionation overhead containing n-pentane and fractionation bottoms containing water;
passing at least a portion of said fractionation overhead containing n-pentane to said second distillation operation;
rectifying at least a portion of said first azeotrope bottoms containing methanol and at least a portion of said aqueous extract containing water and methanol thereby forming a rectification overhead containing methanol; and
passing at least a portion of said rectification overhead containing methanol to said reaction operation.

* * * * *